United States Patent [19]
Sugito

[11] Patent Number: 6,099,515
[45] Date of Patent: Aug. 8, 2000

[54] DISPOSABLE DIAPER

[75] Inventor: Tomoko Sugito, Kagawa-ken, Japan

[73] Assignee: Uni-Charm Corporation, Kawanoe, Japan

[21] Appl. No.: 09/236,071

[22] Filed: Jan. 25, 1999

[30] Foreign Application Priority Data

Jan. 30, 1998 [JP] Japan .................................. 10-020000

[51] Int. Cl.⁷ .................................................. A61S 13/15
[52] U.S. Cl. ........................................................ 604/385.1
[58] Field of Search ............................. 604/385.1, 385.2, 604/378, 379, 358, 365, 367, 374, 375

[56] References Cited

U.S. PATENT DOCUMENTS 5,451,442  9/1995  Pieniak et al. .

FOREIGN PATENT DOCUMENTS

| | | |
|---|---|---|
| 1-141707 | 9/1989 | Japan . |
| 2-26555 | 1/1990 | Japan . |
| 2284931 | 6/1995 | United Kingdom . |
| WO91/09579 | 7/1991 | WIPO . |

*Primary Examiner*—John D. Yasko
*Attorney, Agent, or Firm*—Lowe Hauptman Gopstein Gilman & Berner

[57] ABSTRACT

A disposable diaper includes a liquid-absorbent core which is formed by laminating a fibrous layer principally comprising fluff pulp fibers with a particle layer principally comprising superabsorptive polymer particles. The core is divided along longitudinal lines of the diaper. Each pair of adjacent core divisions present side walls opposed to each other and the particle layer is partially exposed in these side walls.

3 Claims, 3 Drawing Sheets

DISPOSABLE DIAPER

BACKGROUND OF THE INVENTION

This invention relates to a disposable diaper for absorbing and containing body exudates.

Japanese Utility Model Application Disclosure Gazette (Kokai) No. Hei1-141707 discloses a disposable diaper including an absorbent pad divided in a plurality of pad sections. Each pad section comprises a mixture of pulp fibers and superabsorptive polymer. Around each pad section, a topsheet and a backsheet are closely in contact with each other.

In the case of a body fluids absorbent article described in Japanese Patent Application Disclosure Gazette (Kokai) No. Hei2-26555, a mixture of polymer having the property of swelling as it absorbs water and liquid adhesive is intermittently applied to a first liquid-pervious nonwoven fabric so as to form a plurality of body fluids absorbent unit pads which are then covered with a liquid-pervious second nonwoven fabric and these first and second nonwoven fabrics are bonded to each other around the respective unit pads.

These well known techniques make it possible to position the absorbent polymer in a desired region of a disposable diaper or the other body fluids absorbent articles.

Superabsorptive polymer particles as the typical form of the absorbent polymer used in the well known techniques as have been mentioned above swell, soften and aggregate to form a gel block as they absorb water. Such gel block obstruct water permeation and, in consequence, the absorbent material covered with such gel block can no more utilized though the water absorption capacity of the material is still not saturated. Both the pad sections and the unit pads according to the prior art are also inevitably accompanied with such problem. Specifically, the absorbent polymer being present in the proximity of their surfaces may form the gel block and obstruct water permeation into these pad sections or unit pads. Accordingly, an amount of the absorbent polymer or the other absorbent material used in such disposable diaper or the other body fluids absorbent articles of prior art will not be satisfactorily paid.

SUMMARY OF THE INVENTION

In view of the problem as has been mentioned above, it is an object of the invention to provide a disposable diaper so improved that a liquid absorbent capacity of its liquid-absorbent core containing superabsorptive polymer particles can be effectively utilized.

According to the invention, there is provided a disposable diaper comprising a liquid-pervious topsheet, a liquid-impervious backsheet and a liquid-absorbent core disposed therebetween, defining a front waist region, a rear waist region and a crotch region extending therebetween, wherein the core is at least partially divided along longitudinal lines extending from said front trunk region into said rear trunk region via said crotch region so as to form a plurality of core divisions.

This disposable diaper is characterized by that: the core comprises at least one fibrous layer principally consisting of fluff pulp fibers and at least one particle layer principally consisting of superabsorptive polymer particles, substantially forming a laminate of the fibrous layer and the particle layer underlying the fibrous layer, wherein the particle layer is partially exposed in side walls of the respective core divisions.

According to a preferred embodiment of the invention, the core is divided not only along the longitudinal lines but also along transverse lines extending orthogonally to the first-mentioned imaginary lines.

According to another preferred embodiment of the invention, the topsheet extends downwards along each pair of opposite side walls between each pair of adjacent core divisions so as to be placed upon and bonded to the backsheet.

DESCRIPTION OF THE PREFERRED EMBODIMENTS

Details of a disposable diaper according to the invention will be more fully understood from the description given hereunder with reference to the accompanying drawings.

Figure 1:
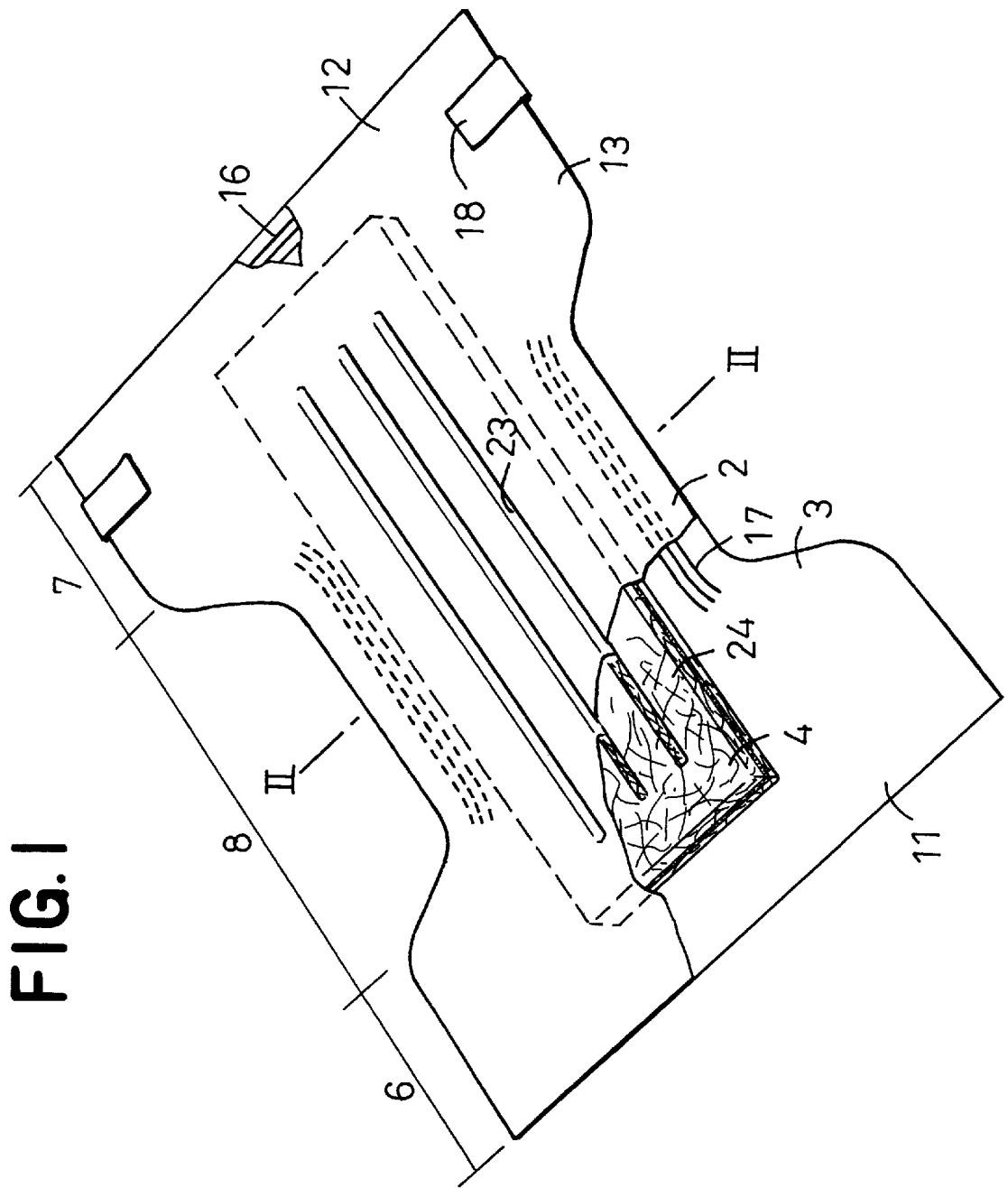
FIG. 1 is a perspective view showing a disposable diaper according to the invention, as partially broken away.

Disposable diaper 1 shown by FIG. 1 in a perspective view as partially broken away comprises a liquid-pervious topsheet 2, a liquid-impervious backsheet 3 and a liquid-absorbent core 4 disposed between these two sheets 2, 3, defining a front waist region 6, a rear waist region 7 and a crotch region 8 extending between these two waist regions 6, 7. The topsheet 2 and the backsheet 3 are bonded to each other along their outward extensions beyond peripheral edges of the core 4 so as to form longitudinally opposite end flaps 11, 12 and a pair of transversely opposite side flaps 13, 13. Along the rear end 12 and the respective side flaps 13, 13, elastic members 16, 17 extending circumferentially of the rear waist region and of the leg-openings, respectively. These elastic members 16, 17 are disposed between the topsheet 2 and the backsheet 3 and secured, under appropriate tensions, to at least one of these topsheet 2 and the backsheet 3. A pair of tape fasteners 18 are attached to the transversely opposite side edges of the rear waist region 7.

Figure 2:
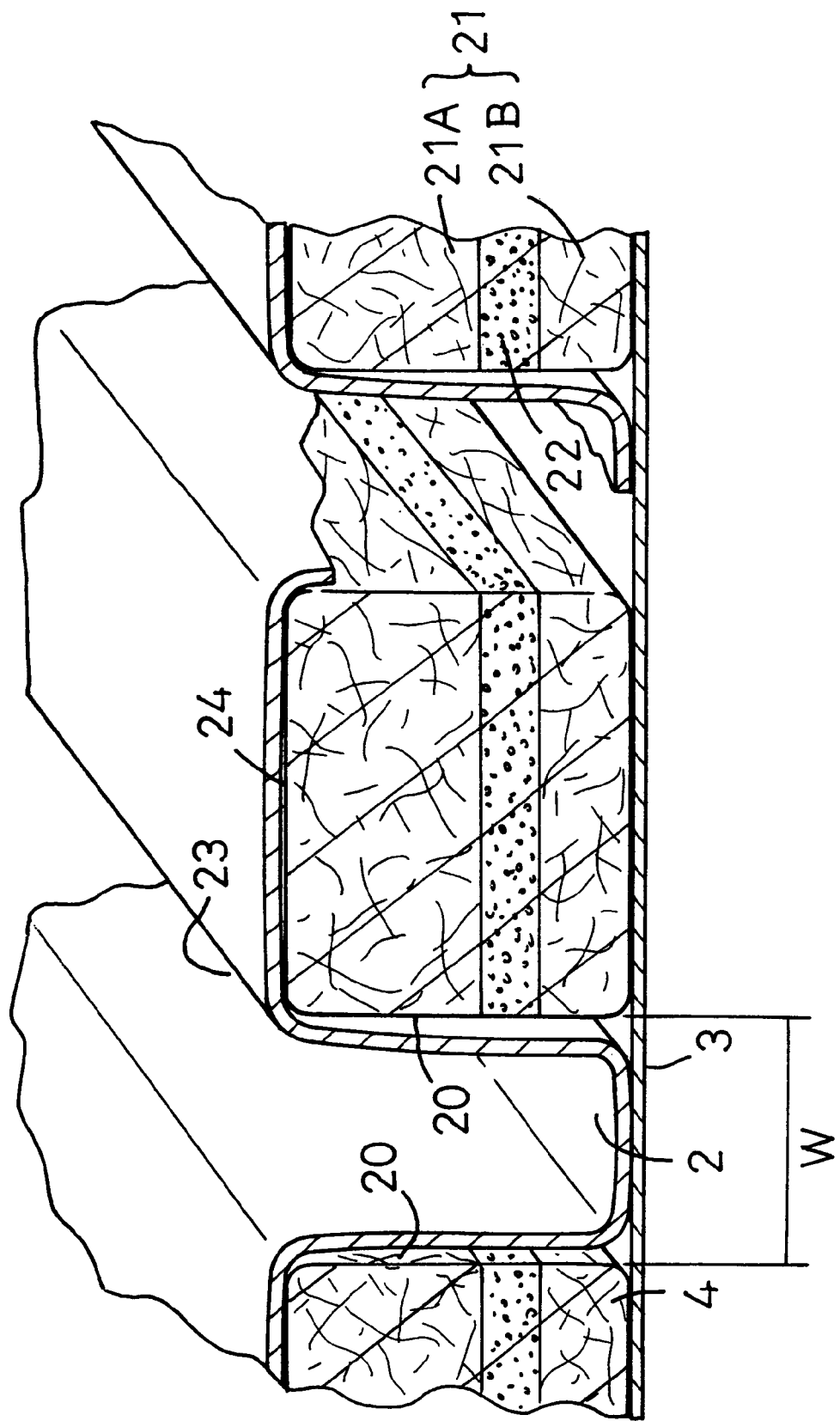
FIG. 2 is a perspective view showing the disposable diaper partially in a sectional view taken along a line II—II in FIG. 1.
Figure 3:
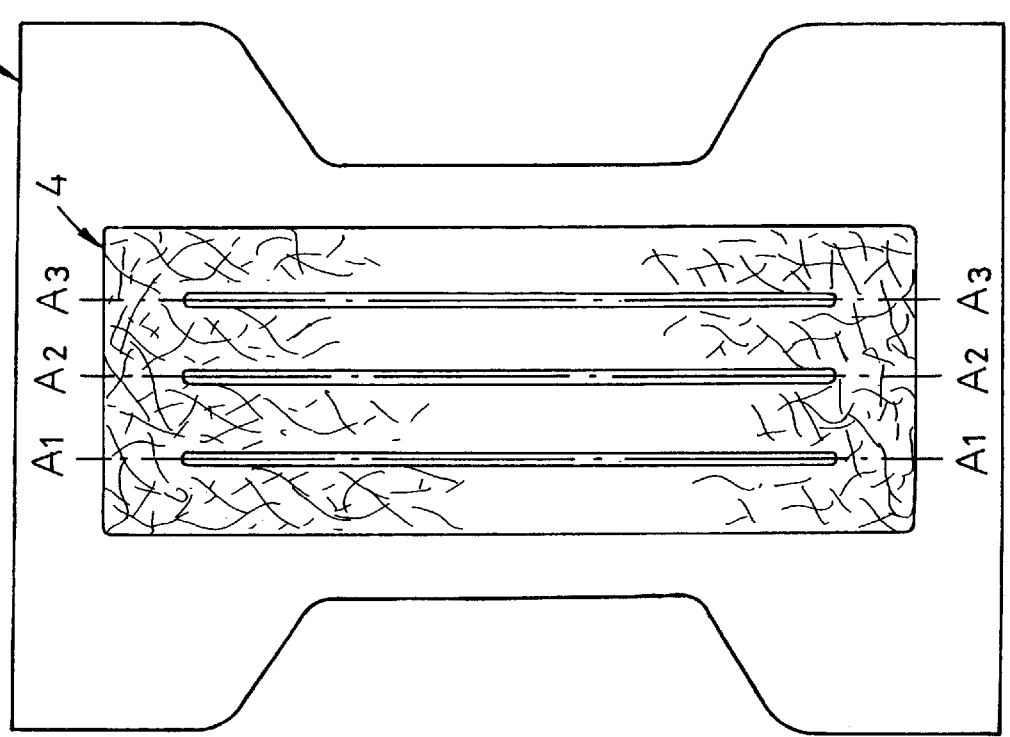
FIG. 3 is a plan view of a liquid-absorbent core as placed upon an inner surface of a backsheet.

FIG. 2 is a perspective view of the diaper 1 partially in a sectional view taken along a line II—II in FIG. 1 and FIG. 3 is a plan view of the core 4. In FIG. 2, the topsheet 2 is shown as partially broken away and, in FIG. 3, the core is shown as placed upon an inner surface of the backsheet 3. The core 4 is provided in the form of a laminate comprising a fibrous layer 21 containing hydrophilic fibers such as fluff pulp fibers of 50 or higher % by weight and a particle layer 22 containing superabsorptive polymer particles of 50 or higher % by weight. Referring to FIG. 2, the fibrous layer 21 includes first and second fibrous layers 21A, 21B between which the particle layer 22 is sandwiched. The first fibrous layer 21A has a thickness equal to or larger than a thickness of the second fibrous layer 21B. More preferably, the thickness of the first fibrous layer 21A is 1.5 or more times of the thickness of the second fibrous layer 21B. The core 4 is partially divided along longitudinally extending lines $A_1$, $A_2$, $A_3$ and each pair of adjacent core divisions are spaced apart from each other transversely of the diaper 1 by a width W. In mutually opposed side walls 20 of these adjacent core divisions, the first and second fibrous layers 21A, 21B as well as the particle layer 22 are partially exposed. Between these opposite side walls 20, the topsheet 2 is guided downwards along the respective side walls 20, placed upon the backsheet and bonded to an inner surface of the backsheet by means of heat-sealing or hot melt adhesive. In this manner, the diaper 1 is formed on its inner side with grooves 23 extending longitudinally of the diaper 1.

With the diaper of such arrangement, body fluids passing through the topsheet 2 are then absorbed by the first fibrous layer 21A through a top surface 24 of the core 4, on one hand, and directly absorbed by the first fibrous layer 21A, the second fibrous layer 21B and the particle layer 22, respectively, through the side walls 20, on the other hand. The particle layer 22 may form gel block as this layer 22 absorbs body fluids and consequently swell and soften. The gel block obstructs smooth transfer of body fluids from the first fibrous layer 21A to the second fibrous layer 21B and prevents the liquid absorbent capacity of the second fibrous layer 21B from being effectively utilized. Even in such case, however, the diaper 1 allows the liquid absorbent capacity of the second fibrous layer 21B to be effectively utilized, since body fluids are absorbed also through the side walls 20 whether the gel block is formed or not.

Figure 4:
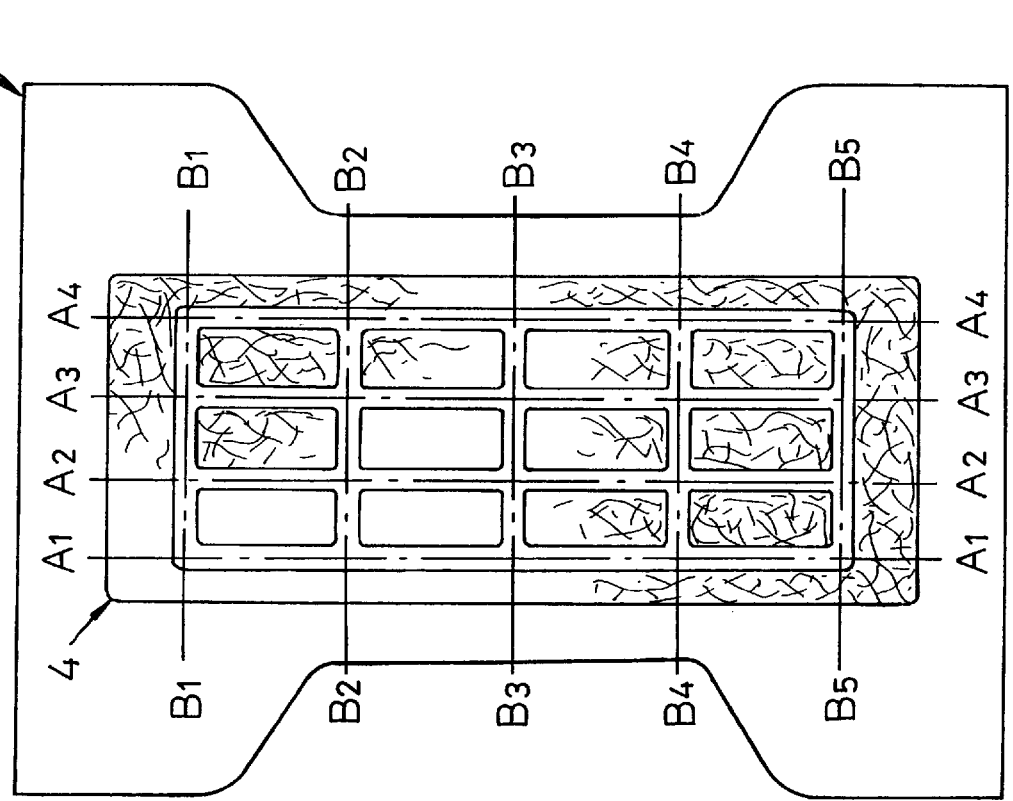
FIG. 4 is a view similar to FIG. 3 showing a specific embodiment of the invention.

FIG. 4 is a view similar to FIG. 3 showing a specific embodiment of the invention. According to this embodiment, the core 4 is divided not only along longitudinally extending lines $A_1 \sim A_4$ but also along transversely extending lines $B_1 \sim B_5$. The topsheet 2 is bonded to the backsheet 3 along the respective lines $A_1 \sim A_4$ and $B_1 \sim B_5$ so that each of the individual core divisions can not be moved independently of the others even though the core 4 is finely divided as shown. The diaper 1 of such arrangement allows a total area occupied by all the side walls 20 of the core 4 to be dimensioned larger than in the case of FIG. 3 and thereby it is possible to improve a body fluids absorption rate as well as an amount by which body fluids can be effectively absorbed.

For exploitation of the invention, the fibrous layer 21 may contain hydrophobic fibers of 0~20% by weight and superabsorptive polymer particles of 0~10% by weight. The hydrophobic fibers contribute to improvement of body fluids diffusibility in the fibrous layer 21. The particle layer 22 may occupy 5~50% by weight of the core 4 and may contain hydrophobic fibers and hydrophilic fibers of 0~50% by weight. The particle layer 22 is preferably sandwiched between the first and second fibrous layers 21A, 21B in order to maintain its form of the layer as shown. Additionally, the particle layer 22 and/or the first and second fibrous layers 21A, 21B preferably have a moisture content of 1~10% by weight in their compressed states. In the core 4 thus compressed, individual fibers may partially extend into the particle layer 22, on one hand, and polymer particles may partially enter into the fibrous layer 21, on the other hand, along interfaces of the respective layers. However, exploitation of the invention never hindered due to such situation. Both the fibrous layer 21 and the particle layer 22 may be respectively multilayered, provided that the uppermost layer of the core 4 is defined by the fibrous layer 21. When the core 4 comprises the fibrous layer covered with a tissue paper, it is also possible to lay the particle layer 22 under the single fibrous layer 21 and then to cover these two layers 21, 22 together with a tissue paper. To facilitate body fluids to flow into the grooves 23 dividing the core 4, a dimension W indicated in FIG. 2 is preferably 1~10 mm. The topsheet 2 may be made of a water-pervious nonwoven fabric or a plastic sheet and the backsheet 3 may be made of a water-impervious plastic sheet.

In the disposable diaper according to the invention, the liquid-absorbent core is the laminate of the fibrous layer principally including fluff pulp fibers and the particle layer comprising superabsorptive polymer particles. This core is divided along the lines extending longitudinally of the diaper and the particle layer is partially exposed in the side walls of the respective core divisions. Accordingly, body fluids are absorbed not only through the top surface of the core but also directly through the side walls into the particle layer and the fibrous layer underlying the particle layer. In other words, the diaper according to the invention allows the liquid absorbent capacity of the particle layer to be efficiently utilized and the liquid absorbent capacity of the fibrous layer underlying the particle layer also to be efficiently utilized even when the particle layer forms gel block.

What is claimed is:

1. A disposable diaper comprising a liquid-pervious topsheet, a liquid-impervious backsheet and a liquid-absorbent core disposed therebetween, defining a front waist region, a rear waist region and a crotch region extending therebetween, wherein said core is at least partially divided along longitudinal lines extending from said front waist region into said rear waist region via said crotch region so as to form a plurality of core divisions, wherein:

said core comprises at least one fibrous layer principally consisting of fluff pulp and at least one particle layer principally consisting of superabsorptive polymer particles, substantially forming a laminate of said fibrous layer and said particle layer underlying said fibrous layer, wherein said particle layer is partially exposed in side walls of the respective core divisions.

2. A disposable diaper according to claim 1, wherein said core is divided not only along said longitudinal lines but also along transverse lines extending orthogonally to the longitudinal lines.

3. A disposable diaper according to claim 1, wherein said topsheet extends downwards along each pair of opposite side walls between each pair of adjacent core divisions so as to be placed upon and bonded to said backsheet.

* * * * *